(12) United States Patent
Oya et al.

(10) Patent No.: US 10,247,695 B2
(45) Date of Patent: Apr. 2, 2019

(54) ELECTRODE FOR GAS SENSOR, AND GAS SENSOR

(71) Applicant: NGK SPARK PLUG CO., LTD., Nagoya, Aichi (JP)

(72) Inventors: Seiji Oya, Niwa-gun (JP); Yuta Oishi, Iwakura (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 13 days.

(21) Appl. No.: 15/702,129

(22) Filed: Sep. 12, 2017

(65) Prior Publication Data

US 2018/0003670 A1 Jan. 4, 2018

Related U.S. Application Data

(62) Division of application No. 14/360,030, filed as application No. PCT/JP2012/007780 on Dec. 4, 2012, now Pat. No. 9,791,404.

(30) Foreign Application Priority Data

Dec. 14, 2011 (JP) .................................. 2011-273369

(51) Int. Cl.
| | |
|---|---|
| *G01N 27/26* | (2006.01) |
| *G01N 27/00* | (2006.01) |
| *G01N 7/00* | (2006.01) |
| *G01N 27/407* | (2006.01) |
| *G01N 27/41* | (2006.01) |

(52) U.S. Cl.
CPC ......... *G01N 27/4075* (2013.01); *G01N 27/41* (2013.01)

(58) Field of Classification Search
CPC ........... G01N 27/26; G01N 27/00; G01N 7/00
USPC .... 422/83, 98, 82.01, 82.02, 90.94; 73/23.2, 73/23.31; 204/424, 426, 431
See application file for complete search history.

(56) References Cited

U.S. PATENT DOCUMENTS

| | | | | |
|---|---|---|---|---|
| 4,579,643 A | * | 4/1986 | Mase | ................... G01N 27/417 204/424 |
| 2011/0083490 A1 | * | 4/2011 | Murakami | ......... G01N 27/4071 73/31.05 |
| 2012/0103059 A1 | * | 5/2012 | Kimata | ................... F01N 11/00 73/23.33 |

* cited by examiner

*Primary Examiner* — Brian J. Sines
(74) *Attorney, Agent, or Firm* — Stites & Harbison, PLLC; Jeffrey A. Haeberlin; James R. Hayne

(57) ABSTRACT

Provided are: an electrode for a gas sensor formed as a porous electrode so as to stably allow reduction in electrode resistance for excellent low-temperature activity; and a gas sensor. The electrode (108, 110) for the gas sensor is adapted for use on a surface of a solid electrolyte body (109), which is predominantly formed of zirconia, and contains particles (2) of a noble metal or an alloy thereof, first ceramic particles (4) of stabilized zirconia or partially stabilized zirconia and second ceramic particles (6) of one or more selected from the group consisting of $Al_2O_3$, MgO, $La_2O_3$, spinel, zircon, mullite and cordierite, wherein the second ceramic particles are contained in an amount smaller than that of the first ceramic particles.

5 Claims, 6 Drawing Sheets

(a)

(b)

ELECTRODE FOR GAS SENSOR, AND GAS SENSOR

FIELD OF THE INVENTION

The present invention relates to an electrode for a gas sensor suitably used to detect the concentration of a specific gas component in e.g. a combustion gas or exhaust gas of a combustion device, internal combustion engine etc. The present invention also relates to a gas sensor.

BACKGROUND ART

There is conventionally used a gas sensor for detecting the concentration of a specific component (e.g. oxygen) in an exhaust gas of an internal combustion engine. This gas sensor includes therein a gas sensor element equipped with at least one cell, each cell having a solid electrolyte body of oxygen-ion-conducting partially stabilized zirconia etc. and a pair of electrodes arranged on the solid electrolyte body. There is also known a gas sensor (such as wide range oxygen sensor, NOx sensor etc.) of the type having two or more cells, one of which is configured as an oxygen pumping cell.

It is common practice to use, as the electrodes of the oxygen pumping cell, porous electrodes each formed with a plurality of pores by adding a vanishable solid material (such as theobromine or carbon) into an electrode paste of noble metal particles and ceramic particles and then sintering the resulting paste (see Patent Document 1). The use of such porous electrodes leads to increase in the three-phase interface between the electrodes, the solid electrolyte body and the air (gas under measurement) for improvement of oxygen pumping performance.

For reduction of power consumption, the gas sensor using the solid electrolyte body is required to have low-temperature activity. In the gas sensor having the oxygen pumping cell, it is particularly required to increase the amount of three-phase interface of the electrodes of the oxygen pumping cell, allow reduction of electrode resistance and improvement of oxygen pumping performance and thereby achieve improved low-temperature activity.

PRIOR ART DOCUMENTS

Patent Documents

Patent Document 1: Japanese Patent No. 4416551

SUMMARY OF THE INVENTION

Problems to be Solved by the Invention

In the case of forming the porous electrodes with the use of the vanishable solid material, however, there are problems such as difficulty of particle size control of the vanishable solid material and variations in the pore size of the formed electrodes. Although the pores are formed in the electrodes due to vanishing of the vanishable solid material at 600 to 800° C., some of the pores are destroyed during the process of temperature rise to a final firing temperature (about 1000 to 1500° C.) so that there occurs variations in the pore size of the finally obtained electrodes. In the case of using theobromine as the vanishable solid material, the theobromine has poor compatibility with solvent and binder so that there also occurs variations in the thickness of the electrodes due to deterioration of leveling (flatness) during the application of the electrode paste. These problems cause variations in the oxygen pumping performance of the electrodes and thereby make it difficult to allow reduction of electrode resistance and achieve improvement of low-temperature activity.

It is accordingly an object of the present invention to provide an electrode for a gas sensor, formed as a porous electrode so as to stably allow reduction of electrode resistance for excellent low-temperature activity. It is also an object of the present invention to provide a gas sensor.

Means for Solving the Problems

In order to solve the above problems, there is provided according to the present invention an electrode for a gas sensor, the gas sensor having a solid electrolyte body predominantly formed of zirconia, the electrode being adapted for use on a surface of the solid electrolyte body, the electrode comprising: particles formed of a noble metal or an alloy thereof; first ceramic particles formed of stabilized zirconia or partially stabilized zirconia; and second ceramic particles formed of one or more selected from the group consisting of $Al_2O_3$, MgO, $La_2O_3$, spinel, zircon, mullite and cordierite, wherein the second ceramic particles are contained in an amount smaller than that of the first ceramic particles.

In the electrode for the gas sensor, the second ceramic particles are brought into contact with the first ceramic particles and deposited on grain boundaries around the first ceramic particles so as to retard the particle growth of the first ceramic particles during sintering. This makes it less likely that the contact points between the first ceramic particles and the predominant noble metal or noble metal alloy particles will be lost during the sintering. It is therefore possible to effectively allow reduction of electrode resistance without decrease in the number of the pores in the electrode (i.e. without decrease in the three-phase interface of the electrode). As the pores are formed in the electrode with the use of no vanishable solid material, it is possible to stably allow reduction of electrode resistance without variations in the diameter and distribution of the pores in the electrode.

The first ceramic particles and the second ceramic particles do not vanish during the sintering. This also leads to less variations in the diameter and distribution of the pores in the electrode. Furthermore, both of the first ceramic particles and the second ceramic particles have good compatibility with solvent and binder for improved dispersibility. This leads to less variations in the thickness of the electrode by improvement of leveling (flatness) during the application of the electrode paste.

In the electrode for the gas sensor, it is preferable that a ratio of the amount of the second ceramic particles to the amount of the first ceramic particles is greater than or equal to 0.1 volume % and less than 50 volume % in order to more effectively allow reduction of electrode resistance without causing deterioration in the adhesion of the electrode.

It is more preferable that, in the electrode for the gas sensor, the ratio of the amount of the second ceramic particles to the amount of the first ceramic particles is greater than or equal to 3 volume % and less than 40 volume % in order to particularly effectively allow reduction of electrode resistance.

It is preferable that an average sintered grain size of the second ceramic particles is 0.1 to 1 time that of the first ceramic particles.

It is preferable that the first ceramic particles are formed of partially stabilized zirconia.

There is also provided according to the present invention a gas sensor comprising: a solid electrolyte body; and a pair of electrodes arranged on the solid electrolyte body, wherein the above-mentioned electrode for the gas sensor is used as each of the pair of electrodes.

There is further provided according to the present invention a gas sensor comprising at least: an oxygen pumping cell having a first solid electrolyte body and a pair of oxygen pumping electrodes arranged on a surface of the first solid electrolyte body; and a detecting cell having a second solid electrolyte body and a pair of detecting electrodes arranged on the second solid electrolyte body, wherein the above-mentioned electrode for the gas sensor is used as each of the pair of oxygen pumping electrodes or each of the pair of detecting cells.

In particular, it is possible to effectively allow reduction of electrode resistance and improvement of oxygen pumping performance and achieve further improved low-temperature activity when the above-mentioned electrode for the gas sensor is used as the oxygen pumping cell.

It is preferable that the electrode for the gas sensor has a thickness of 20 μm or larger for more effective reduction of electrode resistance.

Effects of the Invention

It is possible according to the present invention to stably allow reduction of electrode resistance and achieve improvement of low-temperature activity.

DESCRIPTION OF THE EMBODIMENTS

Hereinafter, embodiments of the present invention will be described below.

Figure 1:
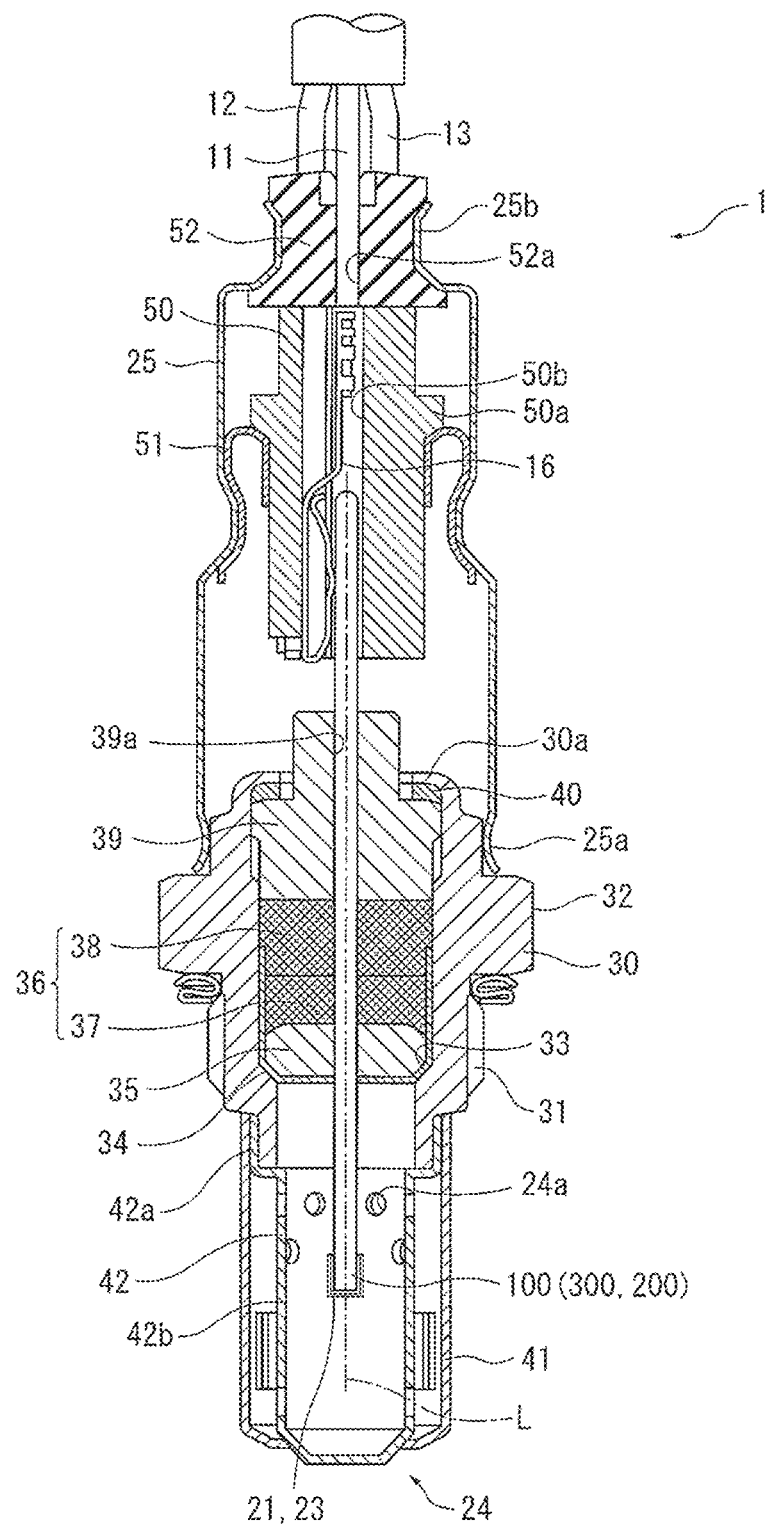
FIG. 1 is a longitudinal section view of a gas sensor (oxygen sensor) according to a first embodiment of the present invention.
Figure 2:
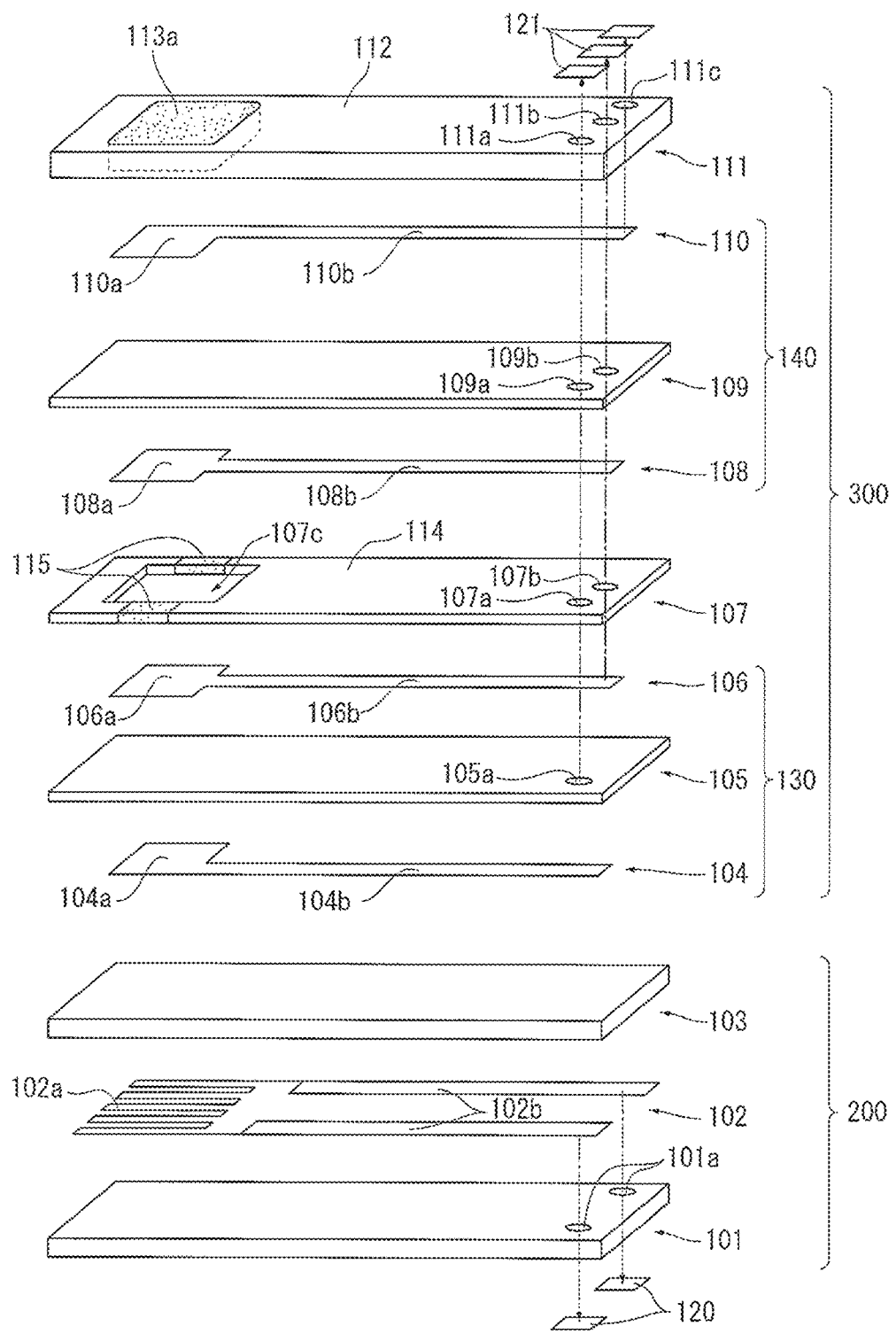
FIG. 2 is a perspective exploded view of a detection element unit and a heater unit of a gas sensor element of the gas sensor according to the first embodiment of the present invention.
Figure 3:
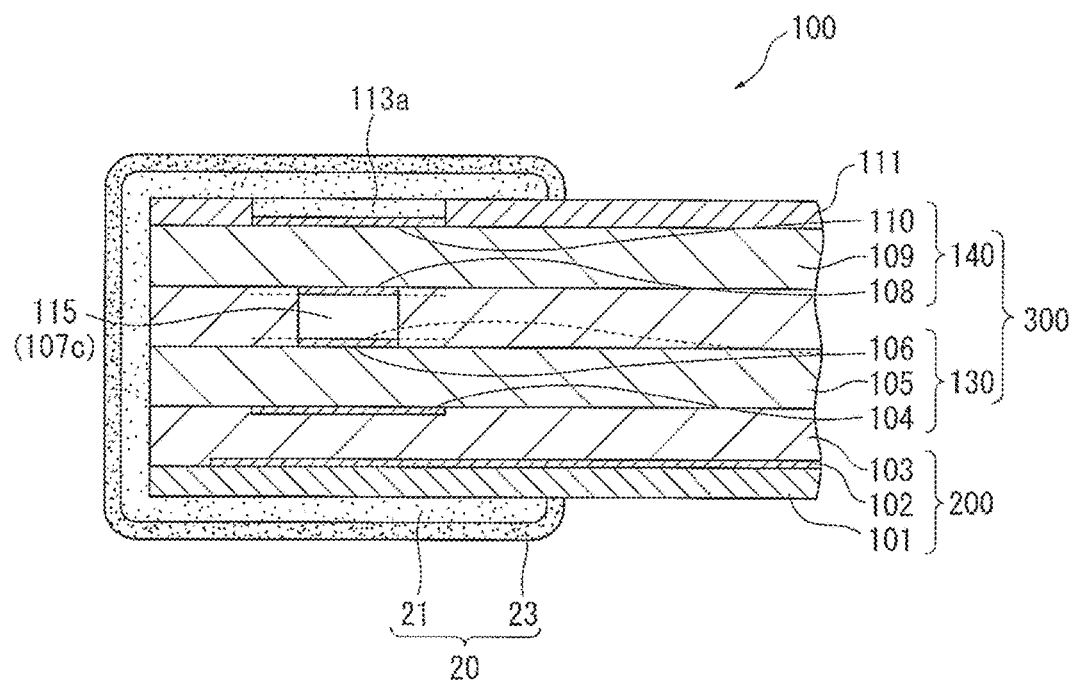
FIG. 3 is an enlarged section view of a front end part of the detection element unit according to the first embodiment of the present invention.

FIG. 1 is a section view of a gas sensor (oxygen sensor) 1, taken in a longitudinal direction (in the direction of an axis L) thereof, according to a first embodiment of the present invention. FIG. 2 is a perspective exploded view of a detection element unit 300 and a heater unit 200 of the gas sensor 1. FIG. 3 is an enlarged section view of the detection element unit 300, taken in a direction perpendicular to the axis L.

As shown in FIG. 1, the gas sensor 1 includes a gas sensor element 100 in which the heater unit 200 is laminated on the detection element unit 300, a metal shell 30 holding therein the gas sensor element 100 and the like and a protector 24 attached to a front end portion of the metal shell 30. The gas sensor element 100 is arranged so as to extend in the direction of the axis L.

The heater unit 200 has first and second substrates 101 and 103 predominantly formed of alumina and a heating member 102 predominantly formed of platinum and sandwiched between the first and second substrates 101 and 103 as shown in FIG. 2. The heating member 102 has a heating portion 102a located on a front end side thereof and a pair of heater lead portions 102b extending from the heating portion 102a in a longitudinal direction of the first substrate 101. Heater-side through holes 101a are formed with conductors in the first substrate 101. Terminal ends of the heater leads 102b are electrically connected to heater-side pads 120 via the conductors of the heater-side through hole 101a, respectively. The laminate of the first and second substrates 101 and 102 herein corresponds to an insulating ceramic body.

The detection element unit 300 has an oxygen concentration detecting cell 130 and an oxygen pumping cell 140. The oxygen concentration detecting cell 130 has a first solid electrolyte body 105 and first and second electrodes 104 and 106 formed on respective opposite surfaces of the first solid electrolyte body 105. The first electrode 104 includes a first electrode portion 104a and a first lead portion 104b extending from the first electrode 104a in a longitudinal direction of the first solid electrolyte body 105. The second electrode 106 includes a second electrode portion 106a and a second lead portion 106b extending from the second electrode portion 106a in the longitudinal direction of the first solid electrolyte body 105.

A first through hole 105a, a second through hole 107a, a fourth through hole 109a and a sixth through hole 111a are formed with respective conductors in the first solid electrolyte body 105, the after-mentioned insulation layer 107, the after-mentioned second solid electrolyte body 109 and the after-mentioned protection layer 111. A terminal end of the first lead portion 104b is electrically connected to a detection-element-side pad 121 through the conductors of the first, second, fourth and sixth through holes 105a, 107a, 109a and 111a. A third through hole 107b, a fifth through hole 109b and a seventh through hole 111b are formed with respective conductors in the after-mentioned insulation layer 107, the after-mentioned second solid electrolyte body 109 and the after-mentioned protection layer 111. A terminal end of the second lead portion 106b is electrically connected to another detection-element-side pad 121 through the conductors of the third, fifth and seventh through holes 107b, 109b and 111b.

The oxygen pumping cell 140 has the solid electrolyte body 109 and third and fourth electrodes 108 and 110 formed on respective opposite surfaces of the solid electrolyte body 109. The third electrode 108 includes a third electrode portion 108a and a third lead portion 108b extending from the third electrode portion 108 in a longitudinal direction of the second solid electrolyte body 109. The forth electrode 110 includes a fourth electrode portion 110a and a fourth lead portion 110b extending from the fourth electrode portion 110a in the longitudinal direction of the second solid electrolyte body 109.

In the first embodiment, each of the third and fourth electrodes 108 and 110 of the oxygen pumping cell 140 corresponds to "an electrode for a gas sensor" as set forth in the scope of claims. As the third and fourth electrodes 108 and 110 are used in the oxygen pumping cell 140, each of the third and fourth electrodes 108 and 110 also corresponds to "an oxygen pumping electrode" as set forth in the scope of claims. As a matter of course, each of the first and second electrodes 104 and 106 can be configured as "an electrode for a gas sensor" as set forth in the scope of claims.

A terminal end of the third lead portion 108b is electrically connected to the detection-element-side pad 121 through the conductors of the fifth and seventh through holes 109b and 111b. An eighth through hole 111c is formed with a conductor in the protection layer 111. A terminal end of the fourth lead portion 110b is electrically connected to another detection-element-side pad 121 through the conductor of the eighth through hole 111c. Herein, the second and third lead portions 106b and 108b are set to the same potential.

Each of the first and second solid electrolyte bodies 105 and 109 is in the form of a sintered body of partially stabilized zirconia material in which yttria ($Y_2O_3$) or calcia (CaO) is added as a stabilizer to zirconia ($ZrO_2$). As the stabilizer added to zirconia ($ZrO_2$), there can be used not only the above mentioned oxide but also $Yb_2O_3$, $Sc_2O_3$, $Gd_2O_3$ or $Nd_2O_3$. The first and second solid electrolyte bodies 105 and 109 may each alternatively be in the form of a sintered body of completely stabilized zirconia material in which the occurrence of modification of zirconia is completely retarded by increasing the amount of the stabilizer added.

Each of the heating member 102, the first and second electrodes 104 and 106, the heat-side pad 120 and the detection-element-side pad 121 are formed of a platinum-group element. As the platinum-group element, Pt, Rh or Pd is preferred. These elements can be used solely or in combination of two or more thereof.

The compositions of the third and fourth electrodes 108 and 110 will be explained later.

It is preferable that the heating member 102, the first and second electrodes 104 and 106, the heat-side pad 120 and the detection-element-side pad 121 are each predominantly formed of Pt in view of heat resistance and oxidation resistance. It is also preferable that each of the heating member 102, the first and second electrodes 104 and 106, the heat-side pad 120 and the detection-element-side pad 121 contains a ceramic component in addition to the predominant platinum-group element component. This ceramic component is preferably of the same as the material of the laminated-side structural part (e.g. the predominant component of the first, second solid electrolyte body 105, 109) in view of adhesion.

The insulation layer 107 is arranged between the oxygen pumping cell 140 and the oxygen concentration detecting cell 130. The insulation layer 107 includes an insulating portion 114 and a diffusion limiting portion 115. A hollow measurement chamber 107c is defined in the insulating portion 114 of the insulation layer 107, at a position corresponding to the second and third electrode portions 106a and 108a, so as to be in communication with the outside in a width direction of the insulation layer 107. In this communication part, the diffusion limiting portion 115 is situated so as to allow gas diffusion between the outside and the measurement chamber 107c under predetermined diffusion-limited conditions.

There is no particular limitation on the material of the insulating portion 114 as long as the insulating portion 114 is in the form of a sintered ceramic body. As the material of the insulating portion 114, there can be used an oxide ceramic material such as alumina or mullite.

The diffusion limiting portion 115 is in the form of a porous body of alumina to limit the flow of gas under measurement into the measurement chamber 107c.

The protection layer 111 is arranged on the surface of the second solid electrolyte body 109 such that the fourth electrode 110 is sandwiched between the second solid electrolyte body 109 and the protection layer 111. The protection layer 111 includes a porous electrode protecting portion 113a covering the fourth electrode portion 110a and protecting the fourth electrode portion 110a from poisoning and a reinforcing portion 112 covering and protecting the fourth lead portion 110b.

In the first embodiment, the gas sensor element 100 is configured as an oxygen sensor element to adjust the direction and magnitude of current flow between the electrodes of the oxygen pumping cell 140 in such a manner as to control the voltage (electromotive force) between the electrodes of the oxygen concentration detecting cell 130 to a predetermined value (e.g. 450 mV), and then, detect the concentration of oxygen in the gas under measurement linearly according to the current flow of the oxygen pumping cell 140.

Figure 4:
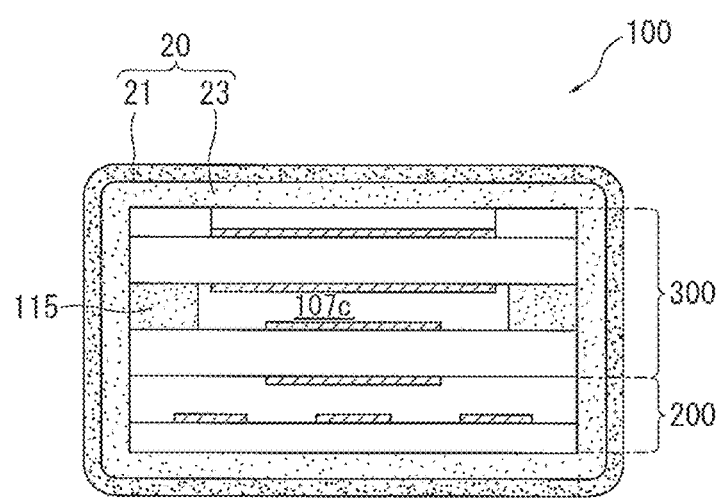
FIG. 4 is a section view of the gas sensor element, taken perpendicular to the direction of an axis of the gas sensor, according to the first embodiment of the present invention.

As shown in FIGS. 3 and 4, the entire circumference of the front end part of the gas sensor element 100 (the laminate of the detection element unit 300 and the heater unit 200) is covered with a porous protection layer 20 (inner and outer porous layers 21 and 23). FIG. 3 is an enlarged section view of the front end part of the gas sensor element 100. FIG. 4 is a section view of the gas sensor element 100 with the inner and outer porous layers 21 and 23, taken in a direction perpendicular to the direction of the axis L.

The inner porous layer 21 is set higher in porosity than the outer porous layer 23. There is a gas-permeable three-dimensional network structure defined by pores of the diffusion limiting portion 115 and the inner and outer porous layers 21 and 23.

Referring back to FIG. 1, the metal shell 30 is formed of SUS 430 and has a male thread portion 31 for mounting the gas sensor into an exhaust pipe and a hexagonal portion 32 for engaging with a mounting tool at the time of mounting of the gas sensor. The metal shell 31 also has a shell-side step portion 33 protruding radially inwardly so as to support thereon a metal holder 34 for holding the gas sensor element 100. A ceramic holder 35 and a talc material 36 are placed in this order from the front end side in the metal holder 34. The talc material 36 includes a first talc material 37 situated within the metal holder 34 and a second talc material 38 situated over a rear end of the metal holder 34. The gas sensor element 100 is fixed to the metal holder 34 by filling and compressing the first talc material 37 in the metal holder 34. Further, the sealing between an outer surface of the gas sensor element 100 and an inner surface of the metal shell 30 is secured by filling and compressing the second talc material 38 in the metal shell 30. A sleeve 39 of alumina is placed on a rear end of the second talc material 38. This sleeve 38 has a multi-diameter cylindrical shape with an axial hole 39a in the direction of the axis so that the gas sensor element 100 is inserted through the axial hole 39a. A rear end crimp portion 30*a* of the metal shell 30 is bent inwardly so as to push the sleeve 39 toward the front via a stainless ring member 40.

The protector 24 is formed of a metal material with a plurality of gas introduction holes 24*a* and welded to an outer circumference of the front end portion of the metal shell 30 so as to cover the front end part of the gas sensor element 100 protruding from the front end of the metal shell 30. This protector 24 has a double-layer structure that consists of a bottomed cylindrical-shaped outer protector member 41 of uniform outer diameter and a bottomed cylindrical-shaped inner protector member 42 formed with a front end portion 42*b* and a rear end portion 42*a* of larger outer diameter than the front end portion 42*b*.

An outer tube 25 of SUS430 is fitted at a front end side thereof around a rear end side of the metal shell 30 by laser welding an enlarged-diameter front end portion 25*a* of the outer tube 25 to the metal shell 30. A separator 50 is arranged in a rear end side of the outer tube 25. A holding member 51 is arranged in a space between the outer tube 25 and the separator 50 and secured with the outer tube 25 and the separator 50 by engaging the holding member 51 with the after-mentioned protruding portion 50*a* of the separator 50 and crimping the outer tube 25.

Through holes 50*b* are formed in the separator 50 from the front end side to the rear end side so that leads 11 to 15 for the detection element unit 300 and the heater unit 200 are inserted through the respective through holes 50*b*. (In the drawings, the leads 24 and 15 are not shown.) Connection terminals 16 are accommodated in the through holes 50*b* for connection to the leads 11 to 15 with the detection-element-side pads 121 of the detection element unit 300 and the heater-side pads 120 of the heater unit 200. The leads 11 to 15 are connected to connectors (not shown) outside of the gas sensor for input and output of electric signals between the leads 11 to 15 and the external device such as ECU through the connectors. Although not specifically shown in the drawings, each of the leads 11 to 15 has a lead wire covered with an insulating coating of resin.

A substantially column-shaped rubber cap 52 is situated in a rear end of the separator 50 so as to close a rear end opening 25*b* of the outer tube 25. The rubber cap 52 is fixed to the outer tube 25 by crimping an outer circumference of the outer tube 25 radially inwardly with the rubber cap 52 fitted in the rear end of the outer tube 25. Through holes 52*a* are also formed in the rubber cap 52 from the front end side to the rear end side so that the leads 11 to 15 are inserted through the respective through holes 52*a*.

The characteristic configuration of the electrode for the gas sensor according to the present invention (in the first embodiment, the third and fourth electrodes 108 and 110) will be explained below with reference to FIGS. 5 and 6.

As mentioned above, porous electrodes each formed with a plurality of pores by adding a vanishable solid material (such as theobromine or carbon) to an electrode paste and sintering the resulting paste are commonly used as electrodes for a gas sensor. There is however a problem that it is difficult to allow reduction of electrode resistance due to variations in the diameter and distribution of the pores in the porous electrodes.

Figure 5:
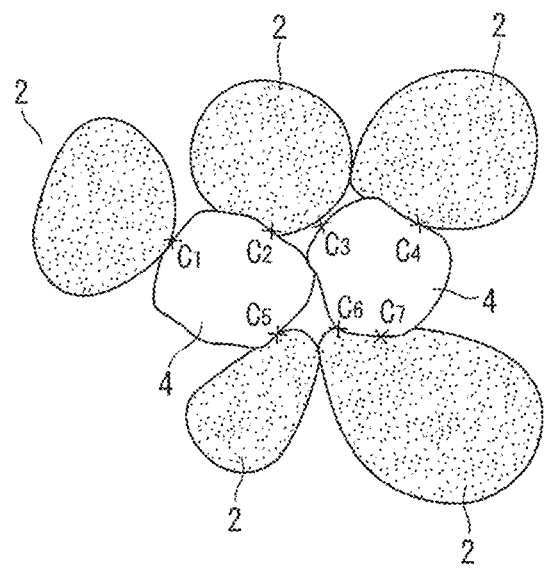
FIG. 5 is a schematic view showing the progress of sintering of an electrode paste containing noble metal particles and first ceramic particles with no vanishable solid material
Figure 5:
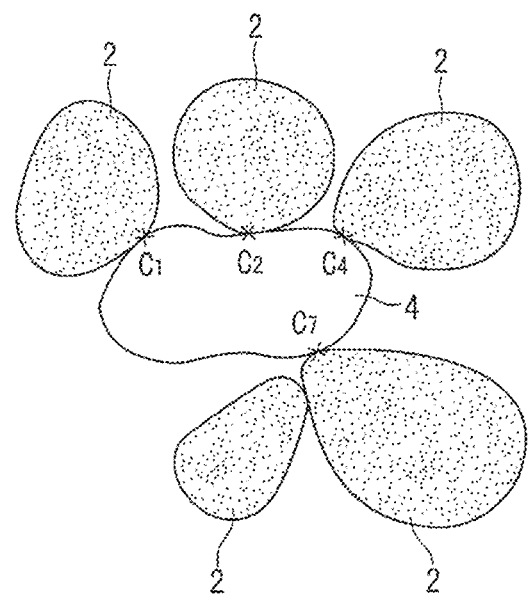
Figure 6:
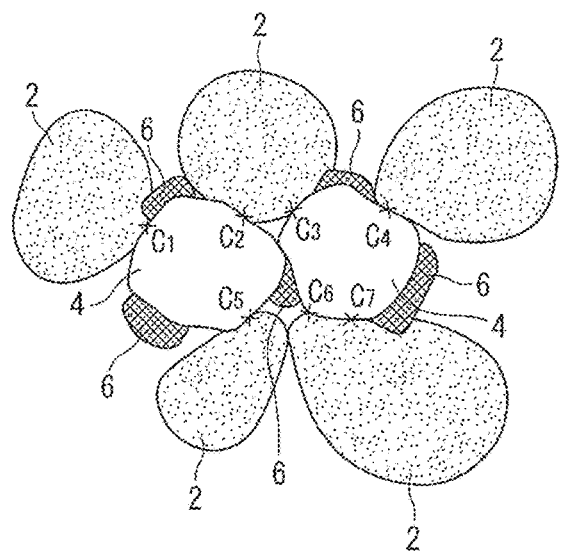
FIG. 6 is a schematic view showing the progress of sintering of an electrode paste containing second ceramic particles in addition to noble metal particles and first ceramic particles.

In the case of sintering an electrode paste containing noble metal particles 2 of noble metal or alloy thereof and first ceramic particles 4 of solid electrolyte with no distinguishable solid material as shown in FIG. 5, for example, two first ceramic particles 4 are brought into contact with each other and, at the same time, brought into contact with five noble metal particles 2 (see FIG. 5(*a*)) in the early stage of sintering. There thus occur total seven contact points $C_1$ to $C_7$ between the two first ceramic particles 4 and the five noble metal particles 2. These contact points $C_1$ to $C_7$ constitute a three-phase interface. With the progress of sintering, however, the first ceramic particles 4 are bonded to each other and grown to a coarse particle so that some of the contact points $C_1$ to $C_7$ are lost (that is, the contact points are reduced to four ($C_1$, $C_2$, $C_4$ and $C_7$)) (see FIG. 5(*b*)). In this way, the particle growth of the first ceramic particles 4 proceeds without the use of the vanishable solid material so as to cause decrease in the number of the pores and, by extension, decrease in the three-phase interface and thereby fail to allow reduction of electrode resistance.

In the first embodiment, second ceramic particles 6 are added to the electrode paste. During the sintering of the electrode paste, the second ceramic particles 6 are brought into contact with the first ceramic particles 4 and deposited on grain boundaries around the first ceramic particles 4 so as to retard the particle growth of the first ceramic particles 4 as shown in FIG. 6. This makes it less likely that the contact points (C1 to C7) between the first ceramic particles 4 and the noble metal (or noble metal alloy) particles 2 will be lost during the sintering. It is therefore possible to effectively allow reduction of electrode resistance without decrease in the number of the pores (i.e. without decrease in the three-phase interface). As the pores are formed with the use of no vanishable solid material, it is possible to stably allow reduction of electrode resistance without variations in the diameter and distribution of the pores.

The first ceramic particles 4 and the second ceramic particles 6 do not vanish during the sintering. This also leads to less variations in the diameter and distribution of the pores. Furthermore, both of the first ceramic particles 4 and the second ceramic particles 6 have good compatibility with solvent and binder for improved dispersibility. This leads to less variations in the thickness of the electrode by improvement of leveling (flatness) during the application of the electrode paste.

As the first ceramic particles 4 are formed of oxygen-ion-conducting ceramic material such as stabilized zirconia or partially stabilized zirconia, the above effect can be obtained without decrease in the number of the pores by retarding the particle growth of the first ceramic particles 4. The first ceramic particles 4, if formed of full zirconia (zirconia only), do not show oxygen ion conductivity. In such a case, the resulting electrode do not perform oxygen pumping function even though the pores (three-phase interface) are formed in the electrode. There is no contribution to reduction of electrode resistance even though the particle growth of those ceramic particles is retarded. For this reason, the first ceramic particles 4 are formed of stabilized zirconia or partially stabilized zirconia in the present invention.

In the gas sensor 1, the oxygen pumping cell 140 pumps oxygen in and out from the measurement chamber 107C. It is thus possible to achieve high oxygen pumping performance by reduction of electrode resistance for further improvement of low-temperature activity in the case of forming the third and fourth electrodes 108 and 110 of the oxygen pumping cell 140 from the electrode paste containing the second ceramic particles.

It is herein assumed that, due to a large difference in ion radius between the first ceramic particles 4 and the second ceramic particles 6, the second ceramic particles 6 are difficult to dissolve in the first ceramic particles 4 and thus are deposited on the grain boundaries around the first ceramic particles 4.

There can be used Au, Ag, Pt, Pd, Rh, Ir, Ru or Os as the noble metal of the predominant noble metal particles 2 in the electrode for the gas sensor. There can be used an alloy of one or more of the above noble metal elements as the noble metal alloy of the predominant noble metal particles 2 in the electrode for the gas sensor. Among others, Pt, Pd, Rh, Ir, Ru or Ag is preferred as the noble metal; and an alloy of one or more elements selected from the group consisting of Pt, Pd, Rh, Ir, Ru and Ag is preferred as the noble metal alloy. Specific examples of the noble metal alloy are Pt—Pd alloy, Pt—Rh alloy, Pt—Pd—Rh alloy, Pt—Ru alloy, Pt—Ru—Ir alloy, Pt—Au alloy and Pt—Ag alloy.

The first ceramic particles 4 are preferably formed of the same material as that of the first, second solid electrolyte body 105, 109, i.e., partially stabilized zirconia in which $Y_2O_3$, CaO, $Yb_2O_3$, $Sc_2O_3$, $Gd_2O_3$ or $Nd_2O_3$ is added as a stabilizer to zirconia ($ZrO_2$). It is alternatively feasible to use, as the material of the first ceramic particles 4, completely stabilized zirconia in which the occurrence of modification of zirconia is completely retarded by increasing the amount of the stabilizer added.

The second ceramic particles 6 are formed of one or more selected from the group consisting of $Al_2O_3$, MgO, $La_2O_3$, spinel, zircon, mullite and cordierite. Among others, alumina ceramic such as $Al_2O_3$ is preferred as the material of the second ceramic particles 6 in view of differences in ion radius and crystal structure to the predominant component, i.e., zirconia of the solid electrolyte body.

It is preferable that, in the electrode for the gas sensor, the ratio of the amount of the second ceramic particles 6 contained to the amount of the first ceramic particles 4 contained is greater than or equal to 0.1 volume % and less than 50 volume %. If the ratio of the amount of the second ceramic particles 6 is less than 0.1 volume %, the particle growth of the first ceramic particles 4 may not be sufficiently retarded during the sintering of the electrode so as to cause decrease in the number of the pores and, by extension, decrease in the three-phase interface and result in increase of electrode resistance. If the ratio of the amount of the second ceramic particles 6 exceeds 50 volume %, the particle growth of the first ceramic particles 4 may be excessively retarded so as to cause deterioration in the adhesion of the electrode due to poor bonding between the first ceramic particles 4.

It is more preferable that the ratio of the amount of the second ceramic particles 6 contained to the amount of the first ceramic particles 4 contained is greater than or equal to 3 volume % and less than 40 volume %.

The ratio (volume %) of the amount of the second ceramic particles 6 to the amount of the first ceramic particles 4 can be determined as, in a cross-sectional SEM image of the electrode for the gas sensor, a ratio of the cross-sectional area of the second ceramic particles 6 to the cross-sectional area of the first ceramic particles 4. As the particle growth retarding effect of the second ceramic particles 6 on the first ceramic particles 4 depends on the volume ratio of the second ceramic particles 6 relative to the first ceramic particles 4, the above ratio value "volume %" can suitably be used as an index of the particle growth retarding effect. The ratio of the amount of the second ceramic particles 6 to the amount of the first ceramic particle 4, if given in units of mass %, is difficult to reflect the particle growth retarding effect in the case where there is a large difference in density between the first ceramic particles 4 and the second ceramic particles 6.

Figure 7:
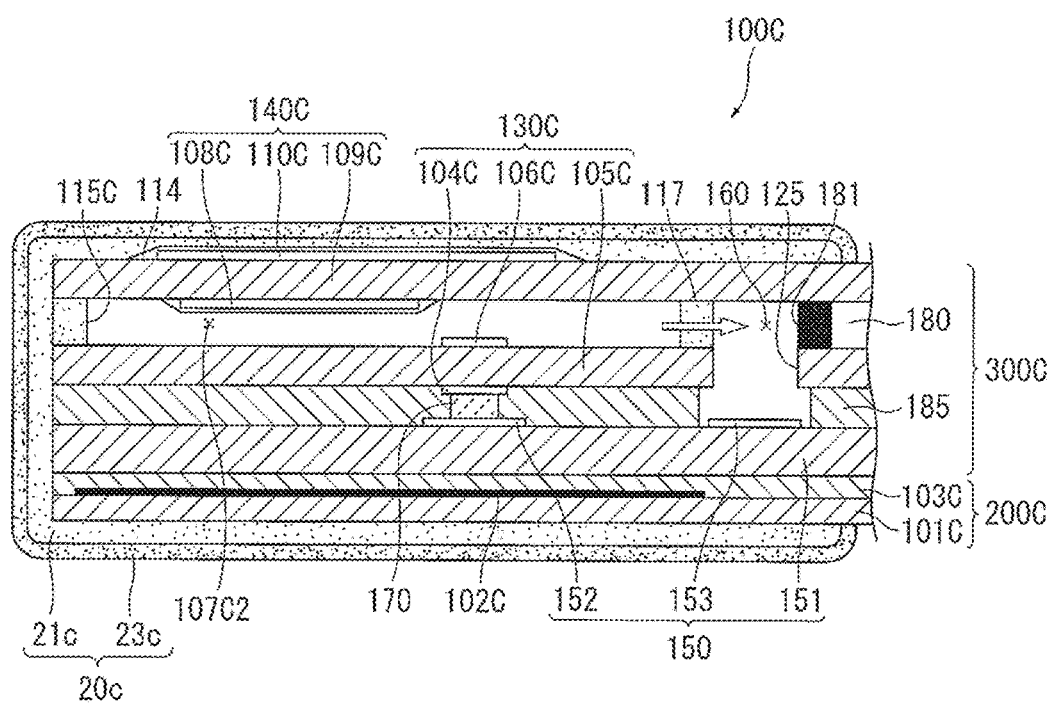
FIG. 7 is a longitudinal section view of a gas sensor element of a gas sensor (NOx sensor) according to a second embodiment of the present invention.

Next, a gas sensor (NOx sensor) according to a second embodiment of the present invention will be described below with reference to FIG. 7. The gas sensor according to the second embodiment is structurally similar to the gas sensor according to the first embodiment, except for the configuration of a gas sensor element 100C. Thus, a description and illustrations of the other structural parts such as metal shell for holding the gas sensor element 100C will be omitted herefrom.

The gas sensor element (NOx sensor element) 100C is formed into an elongated plate shape and has a laminated structure in which insulators 180 and 185 of alumina etc. are laminated between respective adjacent ones of three plate-shaped solid electrolyte bodies 109C, 105C and 151. This laminated structure constitutes a detection element unit 300C. A heater unit 200 is arranged on an outer side of the solid electrolyte body 151 (opposite from the solid electrolyte body 105C in FIG. 1) and includes sheet-like insulation layers 103C and 101C formed predominantly of alumina and laminated to each other and a heater pattern 102C formed predominantly of platinum and embedded between the insulation layers 103C and 101C.

Each of the solid electrolyte bodies 109C, 105C and 151 is in the form of a solid electrolyte body of partially stabilized zirconia (YSZ) and shows oxygen ion conductivity.

The detection element unit 300C is equipped with a first pumping cell (Ip1 cell) 140C, an oxygen concentration detecting cell (Vs cell) 130C and a second pumping cell (Ip2 cell) 150.

The first pumping cell 140C has the second solid electrolyte body 109C and third and fourth electrodes 108C and 110C formed on respective opposite surfaces of the second solid electrolyte body 109C. A porous protection layer 114 of ceramic material is formed on a surface of the fourth electrode 110C so as to protect the fourth electrode 110C from deterioration by exposure to poisoning gas component (reducing atmosphere) of exhaust gas.

The first pumping cell 140C performs the same function as that of the oxygen pumping cell 140 so as to pump oxygen in and out (so called "oxygen pumping") between the after-mentioned first measurement chamber 107C2 and the outside. In the second embodiment, each of the third and fourth electrodes 108C and 110C thus corresponds to "an electrode for a gas sensor" as set forth in the scope of claims.

The oxygen concentration detecting cell 130C has the first solid electrolyte body 105C and first and second electrodes 104C and 106C formed on respective opposite surfaces of the first solid electrolyte body 105C. The above-mentioned first measurement chamber 107C2 and the after-mentioned reference oxygen chamber 170 are separated by the solid electrolyte body 105C. The oxygen concentration detecting cell 130 generates an electromotive force according to a difference in oxygen partial pressure between these chambers 107C2 and 170.

The first measurement chamber 107C2 is defined as a small hollow space between the solid electrolyte bodies 109C and 105C. The second and third electrodes 106C and 108C are placed in the first measurement chamber 107C2. It is herein noted that the first measurement chamber 107C2 is the small space to which the gas under measurement is first introduced from the outside within the gas sensor element 100C.

A porous first diffusion limiting portion 115C is situated in a front end side of the first measurement chamber 107C2 of the gas sensor element 100C and lies between the first measurement chamber 107C2 and the outside so as to limit the flow of the gas under measurement into the first measurement chamber 107C2.

A second diffusion limiting portion 117 is situated in a rear end side of the first measurement chamber 107C2 of the gas sensor element 100C, as a partition between the first measurement chamber 107C2 and an opening 181 to the after-mentioned second measurement chamber 160, so as to limit the diffusion of the gas.

The second pumping cell 150 has the third solid electrolyte body 151 and fifth and sixth electrodes 152 and 153 formed on respective opposite surfaces of the third solid electrolyte body 151. The third solid electrolyte body 151 faces the solid electrolyte body 105C so as to sandwich the insulator 185 therebetween. The insulator 185 is not arranged in a space between the solid electrolyte bodies 151 and 105C in which the fifth electrode 152 is located. This independent space is defined as the reference oxygen chamber 170. The first electrode 104C of the oxygen concentration detecting cell 130C is also located in the reference oxygen chamber 170. The reference oxygen chamber 170 is filled with a porous ceramic material. Further, the insulator 185 is not arranged in a space between the solid electrolyte bodies 151 and 105C in which the sixth electrode 156 is located. This independent small hollow space is defined as the second measurement chamber 160. Openings 125 and 141 are formed in the solid electrolyte body 105C and the insulator 180, respectively, so as to be in communication with the second measurement chamber 160. The first measurement chamber 107C2 and the opening 181 are connected to each other via the second gas diffusion layer 117 as mentioned above.

The reference oxygen chamber 170 and the second measurement chamber 160 are separated by the insulator 185. The second pumping cell 150 pumps oxygen in and out between these chambers 170 and 160.

Further, the entire circumference of the front end part of the gas sensor element 100C (the laminate of the detection element unit 300C and the heater unit 200C) is covered with a porous protection layer 20C (inner and outer porous layers 21C and 23C).

In the second embodiment, the third and fourth electrodes 108C and 110C are each formed as the electrode for the gas sensor by adding the second ceramic particles 6 to the electrode paste and sintering the resulting electrode paste so as to retard the particle growth of the first ceramic particles 4. This makes it less likely that the contact points between the first and second ceramic particles 4 and 6 and the noble metal (or noble metal alloy) particles 2 will be lost during the sintering. It is therefore possible to allow reduction of electrode resistance without decrease in the number of the pores (i.e. without decrease in the three-phase interface). As the pores are formed without the use of the vanishable solid material, it is possible to stably allow reduction of electrode resistance without variations in the diameter and distribution of the pores.

The NOx concentration detection operation of the NOx sensor element 100C will be next briefly explained below.

First, the oxygen pumping cell 140C pumps oxygen in and out between the first measurement chamber 107C2 and the outside in such a manner that the potential difference between the electrodes 104C and 106C becomes constant at around 425 mV.

After the oxygen concentration of the exhaust gas in the first measurement chamber 107C2 is adjusted as mentioned above, the exhaust gas is introduced from the first measurement chamber 107C2 to the second measurement chamber 160 through the second gas diffusion layer 117. Then, NOx in the exhaust gas is brought into contact with the sixth electrode 153 within the second measurement chamber 160 and decomposed (reduced) to $N_2$ and $O_2$ by the catalytic action of the sixth electrode 153. The thus-generated oxygen is converted to oxygen ions upon receipt of electrodes from the sixth electrode 153. These oxygen ions flow through the third solid electrolyte body 151 and move to the fifth electrode 152. At this time, the remaining unpumped oxygen in the first measurement chamber 107C2 is moved to the reference oxygen chamber 170 by the Ip2 cell 150 in the same manner as above. Consequently, there occur a flow of current through the Ip2 cell 150, which includes current derived from the NOx and current derived from the remaining oxygen.

The current derived from the remaining oxygen can be regarded as substantially constant because the concentration of the remaining unpumped oxygen in the first measurement chamber 107C2 has been adjusted to a predetermined value as mentioned above. The current derived from the remaining oxygen has less influence on the current flowing through the Ip2 cell 150 than variations in the current derived from the NOx. The current flowing through the Ip2 cell 150 is thus proportional to the NOx concentration.

The present invention is not limited to the above embodiments. The present invention can be applied to any electrodes for gas sensors using solid electrolyte bodies. In the present invention, it is feasible to use the electrode for the gas sensor in any type of gas sensor. The use of the electrode is not limited to the above-embodied oxygen sensor (oxygen sensor element) and NOx sensor (NOx sensor element). Various modifications and equivalents are possible as long as they fall within the scope of the invention. For example, the electrode can be used in a HC sensor (HC sensor element) for detecting the concentration of HC. Moreover, the use of the electrode is not limited to the above-embodied two-cell-type gas sensor. The electrode can also be used in one-cell-type gas sensor.

EXAMPLES

A gas sensor element of Example 1 will be explained below.

Samples of the plate-shaped gas sensor element (wide-range air/fuel ratio sensor element) 100 shown in FIGS. 1 to 4 were produced. Herein, each of the third and fourth electrodes 108 and 110 of the oxygen pumping cell 140 was configured as "an electrode for a gas sensor".

An electrode paste was first prepared by mixing Pt particles, first and second ceramic particles of the composition shown in TABLE 1, a binder (ethyl cellulose) and a solvent (butyl carbitol) together.

The average grain size of the sintered particles of each type shown in TABLE 1 was determined from a cross-sectional SEM image of the electrode for the gas sensor. More specifically, a cross section of the electrode was observed by a SEM with a magnification of the order of 3500 times. The particles of each type were sketched in the SEM image. The total cross-sectional area of the particles of each type was obtained by analysis of the SEM image. Then, the area ((SA) per particle of each type) was calculated by dividing the total cross-sectional area of the particles of each type by the number of the particles of each type. The diameter of the circle equivalent to the area was determined as the average grain size. These parameters can be represented by the following expressions (1) and (2).

Area per particle of each type($SA$)=Total area of particles of each type/Number of particles of each type     (1)

Average grain size of particles of each type$(DA) = 2 \times \sqrt{(SG/\pi)}$   (2)

In TABLE 1, the content (wt %) of the first ceramic particles refers to the amount of the first ceramic particles contained relative to the amount of the Pt particles; and the content (vol %) of the second ceramic particles refers to the amount of the second ceramic particles relative to the amount of the first ceramic particles.

The third and fourth electrodes 108 and 110 were each produced by applying the electrode paste to appropriated areas of the respective opposite surfaces of the second solid electrolyte body 109, drying the applied electrode paste and sintering the dried electrode paste at a predetermined temperature (1000° C. or higher)

The gas sensor element 100 was obtained by forming the other structural parts as appropriate.

The gas sensor element 100 was tested for the oxygen pumping performance, by mounting the gas sensor element 100 to the gas sensor 1, setting the temperature of the oxygen pumping cell 140 to 700° C. and measuring a Cole-Cole Plot of the electrode resistance between the third and fourth electrodes 108 and 110 (electrode area: 5 mm$^2$). The conditions of measurement of the electrode resistance were as follows: application voltage: 100 mV; and frequency: 0.1 Hz to 100,000 Hz. The rate of reduction of the electrode resistance determined from the Cole-Cole Plot relative to that of Comparative Example 1 was determined. The oxygen pumping performance was evaluated as: "Δ" when the rate of reduction of the electrode resistance was less than 10% (including the case where the electrode resistance was increased relative to that of Comparative Example 1); "○" when the rate of reduction of the electrode resistance was greater than or equal to 10% and less than 20%; and "⊚" when the rate of reduction of the electrode resistance was greater than or equal to 20%.

Further, the adhesion of the electrode was tested by subjecting the gas sensor 1 to 30,000 cycles of on-off operations between room temperature and 800° C. under a normal control state of the gas sensor 1. After the above cycle test, the pumping voltage (Vp) between the third and fourth electrodes 108 and 110 was measured. The rate of increase of the pumping voltage (Vp) relative to that of Comparative Example 1 was determined. The adhesion of the electrode was evaluated as: "Δ" when the rate of increase of the pumping voltage (Vp) 5% or more; and "○" when the rate of increase of the pumping voltage (Vp) less than 5%.

The same evaluation tests as in Example 1 were also performed in Examples 2 to 23. The evaluation results are shown in TABLE 1.

TABLE 1

| | Electrode | | | | | | | | |
|---|---|---|---|---|---|---|---|---|---|
| | Composition | | | | | | | | |
| | | First ceramic particles | | | Second ceramic particles | | | Evaluation | |
| | Noble metal particles | Kind | Average sintered grain size (μm) | Content (wt %) relative to noble metal particles | Kind | Average sintered grain size (μm) | Content (vol %) relative to first ceramic particles | Thickness (μm) | Oxygen pumping performance | Electrode Adhesion |
| Comparative Example 1 | Pt | 8 mol % Y$_2$O$_3$—ZrO$_2$ | 0.8 | 16 | — | — | — | 10 | — | — |
| Example 1 | Pt | 8 mol % Y$_2$O$_3$—ZrO$_2$ | 0.8 | 16 | Al$_2$O$_3$ | 0.07 | 10 | 10 | Δ | ○ |
| Example 2 | Pt | 8 mol % Y$_2$O$_3$—ZrO$_2$ | 0.8 | 16 | Al$_2$O$_3$ | 0.85 | 10 | 10 | ○ | Δ |
| Example 3 | Pt | 8 mol % Y$_2$O$_3$—ZrO$_2$ | 0.8 | 16 | Al$_2$O$_3$ | 0.4 | 0.08 | 10 | Δ | ○ |
| Example 4 | Pt | 8 mol % Y$_2$O$_3$—ZrO$_2$ | 0.8 | 16 | Al$_2$O$_3$ | 0.4 | 53 | 10 | ○ | Δ |
| Example 5 | Pt | 8 mol % Y$_2$O$_3$—ZrO$_2$ | 0.8 | 16 | Al$_2$O$_3$ | 0.4 | 10 | 12 | ○ | ○ |
| Example 6 | Pt | 8 mol % Y$_2$O$_3$—ZrO$_2$ | 0.8 | 16 | Al$_2$O$_3$ | 0.4 | 1 | 12 | ○ | ○ |
| Example 7 | Pt | 8 mol % Y$_2$O$_3$—ZrO$_2$ | 0.8 | 16 | Al$_2$O$_3$ | 0.4 | 10 | 21 | ⊚ | ○ |
| Example 8 | Pt | 5.4 mol % Y$_2$O$_3$—ZrO$_2$ | 0.8 | 16 | Al$_2$O$_3$ | 0.4 | 10 | 12 | ⊚ | ○ |
| Example 9 | Pt | 8 mol % Y$_2$O$_3$—ZrO$_2$ | 0.8 | 16 | Al$_2$O$_3$ | 0.08 | 0.1 | 12 | ○ | ○ |
| Example 10 | Pt | 8 mol % Y$_2$O$_3$—ZrO$_2$ | 0.8 | 16 | Al$_2$O$_3$ | 0.8 | 50 | 12 | ○ | ○ |
| Example 11 | Pt | 8 mol % Y$_2$O$_3$—ZrO$_2$ | 0.8 | 16 | MgO | 0.4 | 10 | 12 | ⊚ | ○ |
| Example 12 | Pt | 8 mol % Y$_2$O$_3$—ZrO$_2$ | 0.8 | 16 | La$_2$O$_3$ | 0.4 | 10 | 12 | ⊚ | ○ |
| Example 13 | Pt | 8 mol % Y$_2$O$_3$—ZrO$_2$ | 0.8 | 16 | spinel | 0.4 | 10 | 12 | ⊚ | ○ |
| Example 14 | Pt | 8 mol % Y$_2$O$_3$—ZrO$_2$ | 0.8 | 16 | zircon | 0.4 | 10 | 12 | ⊚ | ○ |
| Example 15 | Pt | 8 mol % Y$_2$O$_3$—ZrO$_2$ | 0.8 | 16 | mullite | 0.4 | 10 | 12 | ⊚ | ○ |
| Example 16 | Pt | 8 mol % Y$_2$O$_3$—ZrO$_2$ | 0.8 | 16 | cordierite | 0.4 | 10 | 12 | ⊚ | ○ |
| Example 17 | Pt—Pd | 8 mol % Y$_2$O$_3$—ZrO$_2$ | 0.8 | 16 | Al$_2$O$_3$ | 0.4 | 10 | 12 | ⊚ | ○ |
| Example 18 | Pt—Rh | 8 mol % Y$_2$O$_3$—ZrO$_2$ | 0.8 | 16 | Al$_2$O$_3$ | 0.4 | 10 | 12 | ⊚ | ○ |
| Example 19 | Pt—Ru | 8 mol % Y$_2$O$_3$—ZrO$_2$ | 0.8 | 16 | Al$_2$O$_3$ | 0.4 | 10 | 12 | ⊚ | ○ |
| Example 20 | Pt | 8 mol % Y$_2$O$_3$—ZrO$_2$ | 0.8 | 16 | Al$_2$O$_3$ + MgO | 0.4 | 10 | 12 | ⊚ | ○ |
| Example 21 | Pt | 8 mol % Y$_2$O$_3$—ZrO$_2$ | 0.8 | 16 | Al$_2$O$_3$ | 0.4 | 3 | 12 | ⊚ | ○ |
| Example 22 | Pt | 8 mol % Y$_2$O$_3$—ZrO$_2$ | 0.8 | 16 | Al$_2$O$_3$ | 0.8 | 40 | 12 | ⊚ | ○ |
| Example 23 | Pt | 8 mol % Y$_2$O$_3$—ZrO$_2$ | 0.8 | 16 | Al$_2$O$_3$ | 0.4 | 1 | 21 | ⊚ | ○ |

As shown in TABLE 1, it was possible to obtain not only high oxygen pumping performance under low-temperature conditions (700° C.), i.e., excellent low-temperature activity but also good electrode adhesion in each of Examples 5 to 23 where the electrodes were formed by sintering the electrode paste of the noble metal particles and the first and second ceramic particles and used for the oxygen pumping cell.

On the other hand, the oxygen pumping performance was low under low-temperature conditions (700° C.), that is, the low-temperature activity was poor in Comparative Example 1 where the electrode was formed without the use of the second ceramic particles.

Further, the oxygen pumping performance was low under low-temperature conditions (700° C.), that is, the low-temperature activity was poor in Example 3 where the ratio of the amount of the second ceramic particles to the amount of the first ceramic particles was 0.08 vol %.

In Example 4 where the ratio of the amount of the second ceramic particles to the amount of the first ceramic particles was 53 vol %, the electrode adhesion was poor even though the oxygen pumping performance was high under low-temperature conditions (700° C.). The reason for such poor electrode adhesion is assumed that the bonding between the first ceramic particles was poor due to excessive retardation of the sintering of the first ceramic particles.

It has been shown by these results that it is preferable that the ratio of the amount of the second ceramic particles to the amount of the first ceramic particles is greater than or equal to 1 vol % and less than 50 vol %.

The oxygen pumping performance was higher in Example 21 where the ratio of the amount of the second ceramic particles to the amount of the first ceramic particles was 3 vol % than in Example 6 where the ratio of the amount of the second ceramic particles to the amount of the first ceramic particles was 1 vol %.

The oxygen pumping performance was higher in Example 22 where the ratio of the amount of the second ceramic particles to the amount of the first ceramic particles was 40 vol % than in Example 10 where the ratio of the amount of the second ceramic particles to the amount of the first ceramic particles was 50 vol %.

It has been shown by these results that it is more preferable that the ratio of the amount of the second ceramic particles to the amount of the first ceramic particles is greater than or equal to 3 vol % and less than 40 vol %.

In Example 1 where: the average sintered grain size of the first ceramic particles was 0.8 μm; and the average sintered grain size of the second ceramic particles was 0.07 μm, the oxygen pumping performance was low under low-temperature conditions (700° C.), that is, the low-temperature activity was poor.

In Example 2 where: the average sintered grain size of the first ceramic particles was 0.8 μm; and the average sintered grain size of the second ceramic particle was 0.85 μm, the electrode adhesion was poor even though the oxygen pumping performance was high under low-temperature conditions (700° C.). The reason for such poor electrode adhesion is assumed that the bonding between the first ceramic particles was poor due to excessive retardation of the sintering of the first ceramic particles.

It has been shown by these results that it is preferable that the average sintered grain size of the second ceramic particles is 0.1 to 1 time that of the first ceramic particles.

Further, the oxygen pumping performance was higher under low-temperature conditions (700° C.) in Example 6 where: the ratio of the amount of the second ceramic particles to the amount of the first ceramic particles was 1 vol %; and the thickness of the electrode was 12 μm than in Examples 23 where: the ratio of the amount of the second ceramic particles to the amount of the first ceramic particles was 1 vol %; and the thickness of the electrode was 21 μm.

It has been shown by these results that it is preferable that the thickness of the electrode is 20 μm or larger.

As the materials of the second solid electrolyte body 109 and the third and fourth electrodes 108 and 110 of the oxygen pumping cell 140, stabilized zirconia was used in Examples 1 to 7 and 9 to 23; and partially stabilized zirconia was used in Example 8.

Figure 8:
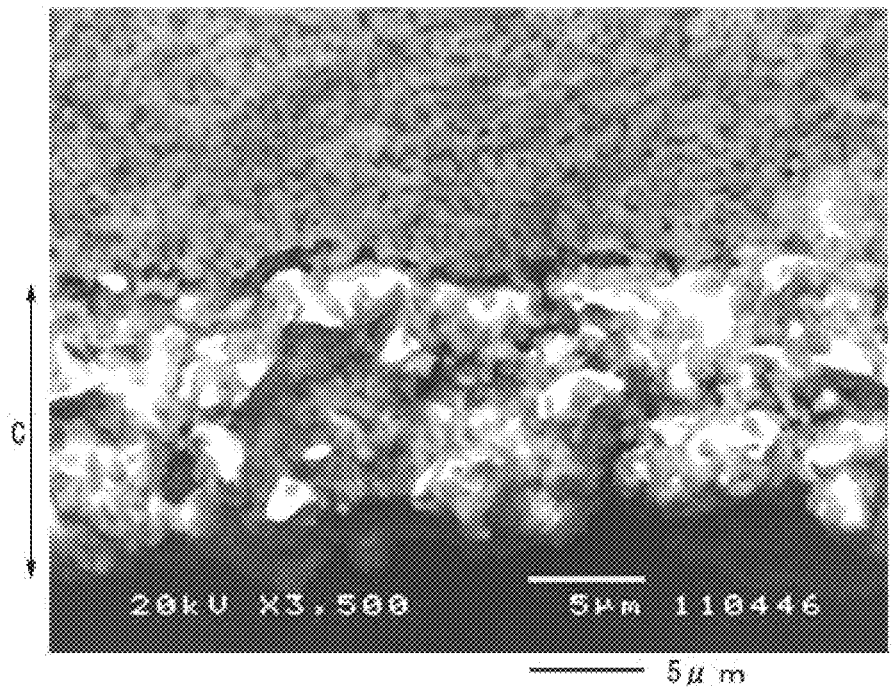
FIG. 8 is a scanning electron microscope (SEM) image showing a cross section of a third electrode of Example 5.
Figure 9:
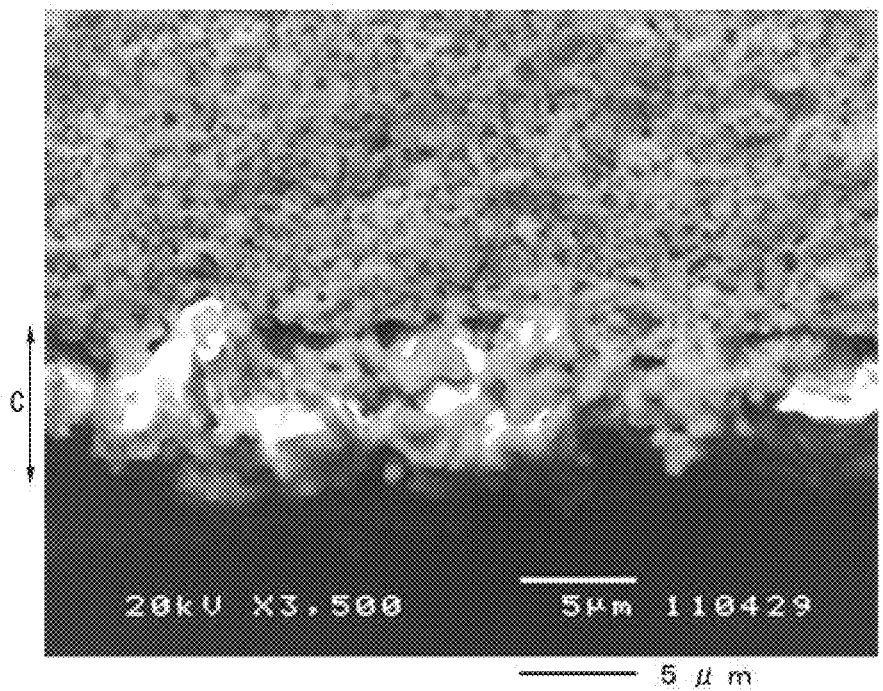
FIG. 9 is a scanning electrode microscope (SEM) image showing a cross section of a third electrode of Comparative Example 1.

FIGS. 8 and 9 are scanning electron microscope (SEM) images showing the cross section C of the third electrode 108 of Example 5 and Comparative Example 1, respectively. Each of the SEM images of FIGS. 8 and 9 is a secondary electron image (composition image) where the grey and white areas of the cross section C correspond to the first ceramic particles and the noble metal (Pt) particles, respectively. In each image, the area above the cross section C corresponds to the solid electrolyte body.

As the grain size of the grey area is smaller in Example 5 than in Comparative Example, it can be confirmed that the particle growth of the first ceramic particles was effectively retarded in Example 5.

DESCRIPTION OF REFERENCE NUMERALS

1: Gas sensor
2: Noble metal particle or noble metal alloy particle
4: First ceramic particle
6: Second ceramic particle
108, 110, 108C, 110C: Electrode for gas sensor
109, 109C: Solid electrolyte body

What is claimed is:

1. A gas sensor comprising: a solid electrolyte body predominantly formed of zirconia; and a pair of electrodes arranged on the solid electrolyte body,
   wherein each of the electrodes comprises:
   particles formed of a noble metal or an alloy thereof;
   first ceramic particles formed of stabilized zirconia or partially stabilized zirconia; and
   second ceramic particles formed of one or more selected from the group consisting of $Al_2O_3$, $MgO$, $La_2O_3$, spinel, zircon, mullite and cordierite; and
   wherein a ratio of an amount of the second ceramic particles to an amount of the first ceramic particles is greater than or equal to 3 volume % and less than 40 volume %.

2. The gas sensor according to claim 1, wherein each of the electrode is an oxygen pumping electrode.

3. The gas sensor according to claim 1, wherein each of the electrodes has a thickness of 20 μm or larger.

4. The gas sensor according to claim 1, wherein an average sintered grain size of the second ceramic particles is 0.1 to 1 time that of the first ceramic particles.

5. The gas sensor according to claim 1, wherein the first ceramic particles are formed of partially stabilized zirconia.

* * * * *